United States Patent [19]

Beck et al.

[11] 4,294,656

[45] Oct. 13, 1981

[54] PROCESS FOR MEASURING THE STATE OF CHARGE OF SUSPENSIONS AND FOR CONTROLLING THE ADDITION OF AUXILIARY AGENTS TO THE SUSPENSIONS

[75] Inventors: Ulrich Beck, Bornheim-Merten; Ekhard Rohloff, Düesseldorf, both of Fed. Rep. of Germany

[73] Assignee: Bayer Aktiengesellschaft, Leverkusen, Fed. Rep. of Germany

[21] Appl. No.: 136,188

[22] Filed: Apr. 1, 1980

Related U.S. Application Data

[63] Continuation of Ser. No. 949,357, Oct. 6, 1978, abandoned.

[30] Foreign Application Priority Data

Oct. 14, 1977 [DE] Fed. Rep. of Germany ....... 2746179

[51] Int. Cl.$^3$ ............................................ D21F 11/00
[52] U.S. Cl. .................................. 162/192; 162/198; 162/183; 162/263
[58] Field of Search ................. 162/49, 183, 192, 148, 162/61, 62, 263; 73/643; 324/425, 441, 439, 450

[56] References Cited

U.S. PATENT DOCUMENTS 3,576,713  4/1971  Fricke ................................. 162/49

OTHER PUBLICATIONS

Beck et al., Tappi, vol. 61, No. 9, pp. 63–65, 9/78.
Zana et al., "The Journal of Physical Chemistry", vol. 71, Nos. 3 & 11, 2-67, 10-67, pp. 521–536 and 3502–3516.
Halabisky, D. D., "Wet End Control for the Effective Use of Cationic Starch," 1977, Papermakers Conference, 4–77.
Kawamura et al., Journal of Amer. Water Works Assoc., 8-67, pp. 1003–1013.

*Primary Examiner*—William F. Smith
*Attorney, Agent, or Firm*—Sprung, Felfe, Horn, Lynch & Kramer

[57] ABSTRACT

When a suspension is exposed to a field of ultrasound, a voltage can be tapped from two electrodes whose distance apart is an odd multiple of half ultrasonic wavelengths, and this voltage can be used as a controlling factor for the addition of, preferably, retention and flocculating agents to the suspension. The process is particularly suitable for fibre suspensions for the purpose of monitoring the starting process in paper machines and for rapid operating control.

6 Claims, 6 Drawing Figures

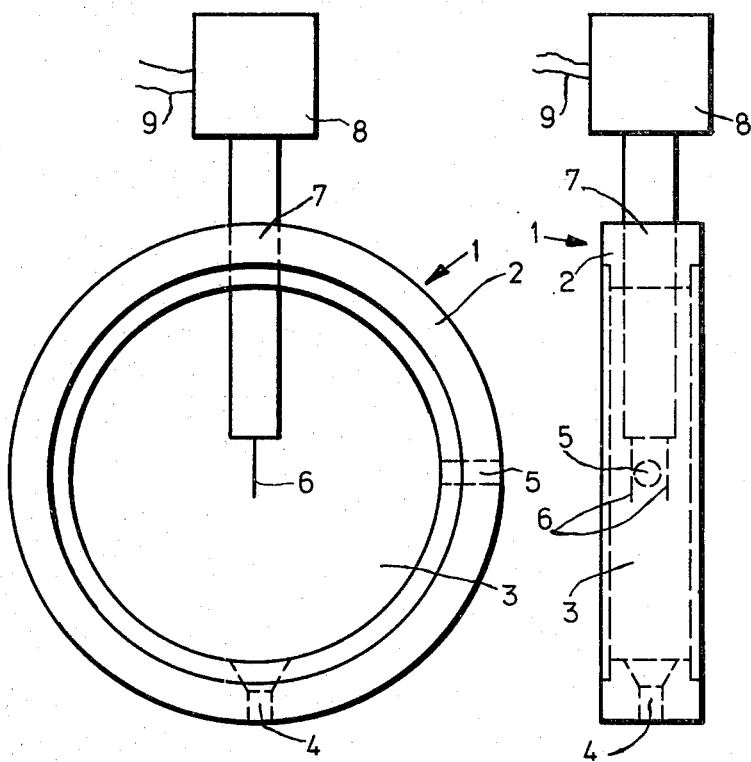
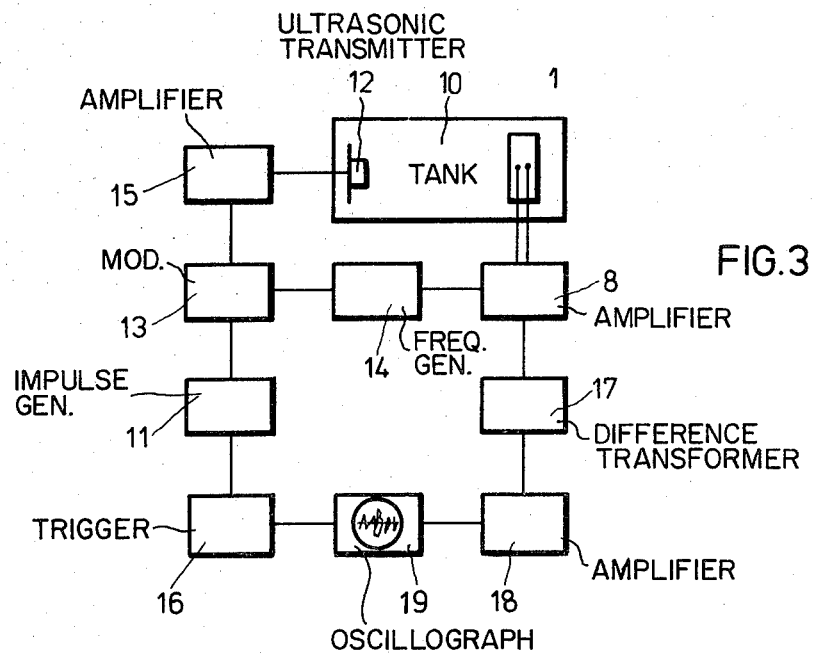
FIG.1  FIG.2
FIG.3

PROCESS FOR MEASURING THE STATE OF CHARGE OF SUSPENSIONS AND FOR CONTROLLING THE ADDITION OF AUXILIARY AGENTS TO THE SUSPENSIONS

This is a continuation, of application Ser. No. 949,357, filed Oct. 6, 1978 abandoned.

The present invention relates to a process for measuring the zetapotential of suspensions and for controlling the addition of auxiliary agents to the suspensions via zetapotential.

The state of charge of the solid particles in a suspension has a considerable influence upon the properties of the suspension. One parameter which characterises the the behaviour of flocculation and retention, is the electrokinetic potential, also known as Zeta potential. The state of and on the zeta potential has particular technical importance in fibre suspensions (cellulose fibres, synthetic fibres, glass fibres inter alia) and in pigment suspensions, and it can be considerably influenced by dissolved or by other suspended substances. The addition of polyvalent salts, surface active agents, polymers or dyes can substantially alter the electrokinetic potential. In the paper industry, it is known that the extent to which the substances added in the wet portion, such as, for example, fillers, dyes and size, adhere to the fibres, in other words are still present on the end product, depends to a considerable extent on the state of charge. The incorporation of the wet portion additives in the web of paper is improved by the addition of so-called retension agents which alter the electrokinetic potential.

The state of charge of a suspension including the effect of the counter ions is determined either from the microelectrophoretic mobility or from the so-called streaming potential. Both are complicated methods of measurement which require qualified staff. Conceptual models and methods of measurement are discussed in "Das Papier" 12 (1975) 514/563. Summarizing, it may be said that simple conceptual models do not fully explain the behaviour of technically important suspensions, that for optimum retention the Zeta potential need not necessarily be zero because the screening of multipolar forces, the change in adsorption behaviour and the blockage of adsorption areas play a role, that not even the direction of the effect of a change in Zeta potential can be predicted with certainty and that scientific investigations carried out on simple model substances have been of only substantially minor importance for the practitioner.

The systematic measurement of relationships such as, for example, the wet breaking length or ash value or opacity in dependence upon the Zeta potential, has up to now only been carried out to a small extent in practice, because measurements of the microelectrophoretic mobility or of the streaming potential are time consuming and therefore it is only possible to take random samples and the method is not suitable for process control. Brief, temporary changes in the state of charge of the suspension in operation, for example during manufacture of a fleece or on a paper machine, could not hitherto be followed by means of measuring techniques. The possibility of utilizing a knowledge of the electric charge distribution in the suspension generating a signal from to improve the manufacturing process has therefore not hitherto been possible.

It is an object of the present invention to measure the electrokinetic potential of solid particles in a suspension by a simple, rapid and as far as possible continuous method, particularly one which also reveals the influence of auxiliary substances and changes in the state of charge of the suspension with time, and the measuring signals should be able to be used in known manner for producing commands to optimise the operation also on a large technical scale.

According to the present invention, there is provided a process for measuring the state of charge of suspensions and controlling the addition of auxiliary agents to the suspensions, wherein a portion of the suspension is exposed to an ultrasonic field in a measuring cell, said measuring cell having two electrodes which extend into the suspension and are spaced from each other by an odd multiple of half ultrasonic wavelengths of the ultrasonic field in the suspension, and generating a signal from the voltage thereby formed between the electrodes which corresponds to the state of charge and determines the addition of auxiliary agent.

The process according to the invention makes use of the fact that in electrolytic solutions, measurable alternating voltages which can be tapped by two electrodes occur in a sufficiently powerful field of ultrasound. The voltage is due to the so-called vibration potential which to a first approximation depends upon the concentration and mass of the particles and is proportional to the Zeta potential. The relationships are described in J. Phys. Chem. 71 (1967) 3502/3516. It has been found that these signals are suitable for controlling the addition of auxiliary agents to fiber suspensions, the addition of which affects the state of the charge. This can ultimately be used to control and obtain optimum flocculation.

The process according to the invention enables the electrokinetic potential to be measured at intervals of less than 10 seconds, i.e. the Zeta potential can be measured virtually continuously. It is advisable to divert a partial stream of the suspension which is to be investigated and by-pass it through the measuring cell, but even if such continuous measurement is not possible, for example because the installation on a machine already provided would be too expensive at the moment, samples of suspension may be removed at brief time intervals and investigated separately. This still enables variations with time to be detected because the individual measurement is very rapid and the removal of samples may be automated if desired.

It may be advisable to dilute the suspension by the addition of liquids, for example distilled water, in order to reduce the effect of inorganic salts (e.g. alum) on the measuring signal. The influence of the retention agent on the zetapotential may then become clearer. A dilution which is maintained constant does not affect the possibility of controlling and optimising the system by means of measurement of the Zeta potential.

The process of measurement according to the invention has proved particularly suitable in the manufacture of paper. When there is an adverse change in the state of charge of a paper pulp, only a small portion of the wet additives adhere to the paper and both the quality of the paper and the economy of the process are very deleteriously affected. Although the sieve water has hitherto been investigated and if the concentration of it was found to increase, retention agents were added with a view to improving the retention, this method of adjustment was two inaccurate, slow and expensive. Moreover, no economically defensible experiments could be carried out on large machines. The process according to the invention provides one relevant, unequivocal figure and the dependence of the state of charge of the suspension on the initial parameters can be investigated relatively easily and rapidly. It is impossible to prevent certain factors of the starting materials fluctuating in some unknown manner during operation. In the process according to the invention, the operator can assess from a strip chart whether the conditions are gradually changing or whether a deterioration in quality is caused by a temporary disturbance. More particularly, the direction of the change can be instantly recognised whereas this information in most cases cannot be obtained from an investigation of the product or of the by-products, for example the measurement of unadsorbed polymer in the effluent.

The optimum electrokinetic potential for a system must be determined by experiments. The process according to the invention does not render laboratory experiments superfluous but can in fact be used very advantageously in the laboratory. Since processes of retention and fluocculation are highly complex, it is advantageous that the rapidity of the method of measuring enables many series of measurements with different various of parameters to be obtained. It is particularly advantageous that the starting processes, in which the product quality is frequently poorer, can be extremely shortened. The process according to the invention is suitable for production control in the manufacture of paper, in particular the manufacture of paper laminates and paper used for labels. Reliable control is possible in principle even with high electrolyte contents (e.g. alum).

Continuous measurement of the vibration potential is also useful in the treatment of effluent. It has been found that with the process according to the invention it is possible to recognise very quickly why there is a change in the quality of effluent and for what purpose other auxiliary substances need to be added, in particular flocculating agents, and why the quantities added must be changed.

The measuring cell must be adjusted to the ultrasonic generator. It must be large enough not to exert an undue influence on the ultrasonic field. The electrodes must be situated diagonally opposite each other in the apices of the sound lobes in order to obtain maximum receiving voltages. The distance between the electrodes is an odd multiple of half ultrasonic wavelengths in the liquid. The acoustic irradiation should be carried out in the remote radiation field of the pulsed ultrasonic transmitter. This necessitates the use of a corresponding path of precession of sound. Superimposition of electromagnetic HF-stray interference and the measuring signal are thereby avoided. The measuring signal is substantially proportional to the Zeta potential.

It is advantageous if a partial stream of the suspension to be investigated continuously flows through the measuring cell although substantially the same effect can also be obtained by taking samples at intervals and carrying out separate measurements. The time intervals depend mainly on the filling and emptying process of the cell.

The signal required for controlling the addition of auxiliary agent may also be obtained from a discrete set of measuring points.

Apart from the speed of measurement, another special practical advantage is the substantially wider range of measurement obtainable in the process according to the invention. The particles may have any form and their size may be within a range of ca. 0.01 $\mu$m to 2 mm. The solid concentration may vary from very small values to about 1%. The vibration potential can also be measured on polyelectrolytes so that a product can be quickly graded according to its "charge characteristic". Preliminary experiments designed to save time and cost can be carried out on practical models in the laboratory.

The sign of the electrokinetic potential is not immediately recognisable in the process according to the invention but can be determined by the addition of auxiliary agents whose effect is known. Difficulties in determining the sign may occur if the values are small (below 30 $\mu$V), but it has so far been found that under optimum conditions the values are in most cases above 100 $\mu$V, in particular in the manufacture of paper.

An apparatus for carrying out the process is illustrated by way of example in the accompanying drawings, in which:

FIG. 1 represents a measuring cell (operating discontinuously) seen from the front;

FIG. 2 represents a measuring cell (operating discontinuously from the side;

FIG. 3 is a block diagram of the measuring apparatus;

Figure 4:
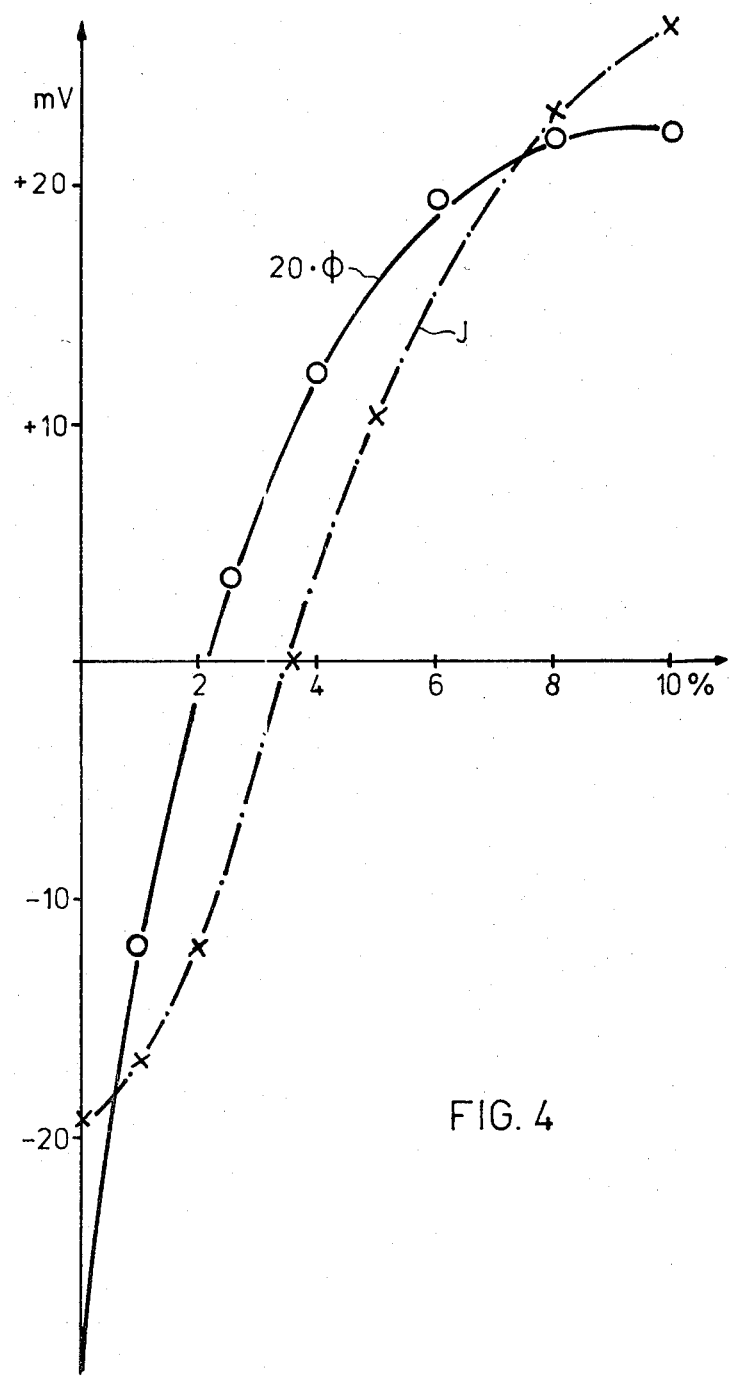
FIG. 4 shows the relationship between the flow potential; the vibration potential and the concentration of retention agent in a cellulose suspension.

A measuring cell 1 is cylindrical. The cylindrical surface 2 is made of Plexiglas (Trade Mark) and the top and bottom 3 of Mylar (Trade Mark) foil. The diameter is 150 mm and the cylinder is approximately 35 mm in height. In this example, the cell is not integral with a paper machine but installed in a separate apparatus. Filling and emptying of cell 1 is carried out through apertures 4 and 5 and takes approximately 30 seconds. The cell is filled to only about 2/3 of its capacity. Two specially insulated platinum wires 6 having a diameter of 0.26 mm dip into the suspension in use. The distance between them, which is ca. 3 mm, is adjusted to the ultrasonic wavelengths in the suspension. An impedance converter, cathode follower amplifier 8 is installed in the upper end of the electrode support 7. The measuring signal is transmitted via wires 9 to signal processing instruments (not shown).

The measuring cell 1 is placed at the end of a tube 10 filled with water. An ultrasonic transmitter 12, a barium titanate crystal 50 mm in diameter, is at a distance of approximately 1.5 m from the measuring cell 1. Its resonance frequency is 200 kHz and the pulse duration is 1.2 msec. The wave travels for approximately 2 msec from transmitter to the cell. The auxiliary devices required for adjustment and tempering are not shown.

The electronic instruments required are illustrated schematically in FIG. 3. A frequency generator 14 can be adjusted to the resonance frequency of the barium titanate crystal 12. The amplitude of the ultrasonic signal between 100 and 800 kHz is modulated at a modulator 13 with a rectangular pulse produced in an impulse generator 11, and the signal is then further amplified at an amplifier 15.

The very small voltage occuring at the platinum electrodes, which is proportional to the vibration potential, is slightly amplified and impedance converted in a cathode follower amplifier 8. The difference signal is then formed from it in a difference transformer 17. This "weak foundation" pulse modulated signal is amplified by a factor of $10^4$ to $10^6$ in an amplifier 18 and indicated on an oscillograph 19. A trigger 16 serves to synchronise production of the ultrasonic signal and reception of the signal.

Figure 5:
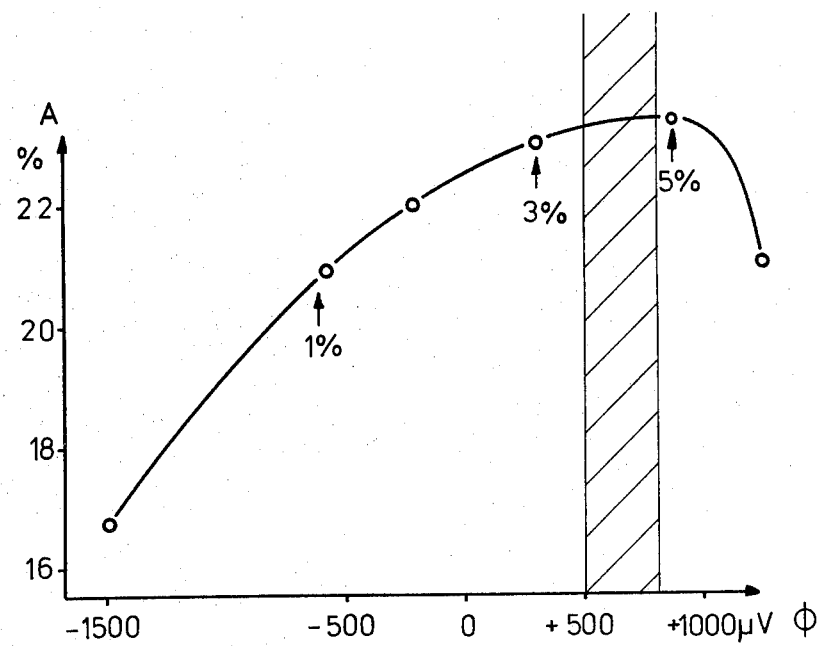
FIG. 5 represents the ash content in dependence upon the vibration potential in laminate paper.
Figure 6:
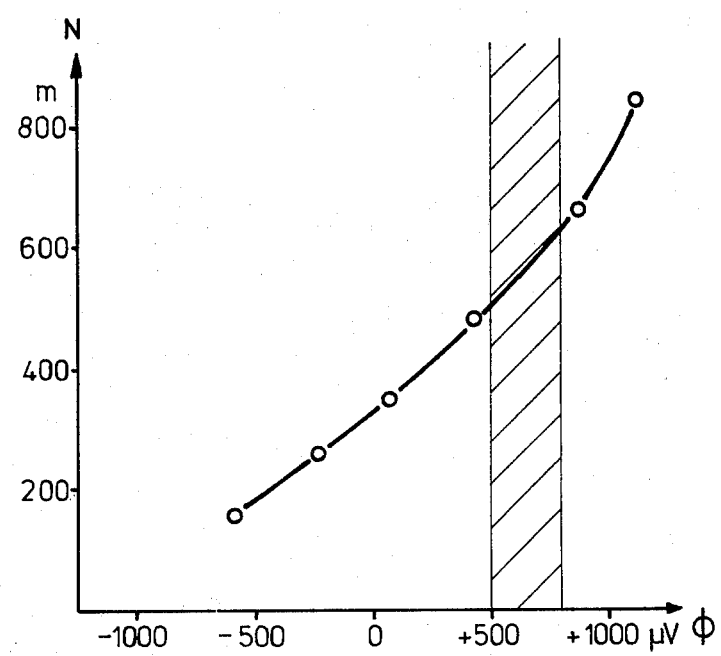
FIG. 6 represents the wet breaking length in dependence upon the vibration potential in laminate paper.

The relationships between the ash content and wet breaking length due to the addition of retention agent measured in such an apparatus are represented in FIGS. 5 and 6. The suspension consists mainly of cellulose, titanium dioxide and wet strengthening agents or retention agents and is almost identical to the paper pulp used for the manufacture of laminate paper.

It is well known that such a system is difficult to stabilise, that is to say it takes hours to obtain constant values of retention, opacity and wet breaking length. With the relatively high quantities of wet strengthening and retention agents and titanium dioxide used, a long starting time is very expensive. These times can be considerably shortened by controlling the system by means of continuous measurement of the Zeta potential.

In FIG. 4, the potential in mV is plotted along the ordinate against the quantity of retention agent (based on the solid content) along the abscissa. A comparison between the measurement of flow potential and the measurement of vibration potential is intended to demonstrate that the two methods provide the same information about the state of charge of the suspension provided the measurements are carried out on the same system. The method of measuring the vibration potential, on the other hand, provides the possibility of much more rapid as well as continuous and variable (as regards particle size and solid concentration) control of production.

The suspension was again modelled on that used for a paper pulp for the manufacture of laminate paper, containing ca. 40% of titanium dioxide by weight of fibre. The material density of the fibres was 0.25%. The retention agent used as Nadavin LT (Trade Mark) and is plotted on the abscissa in % by weight.

FIG. 5 represents the ash content A in % in dependence on the vibration potential in $\mu V$.

FIG. 6 shows the wet tearing length N in meters in dependence upon the vibration potential in $\mu V$.

The finished paper is required to have a wet tearing length of at least 500 m. The ash content of the paper and its opacity should be as high as possible. The optimum range for the given example is from 500 to 750 $\mu V$. Deviation of the system from these values results in substantial losses due to poor quality reject goods. Control of the system by rapid and continuous measurement of the Zeta potential is extremely useful not only for the starting time but also for continous monitoring of the process. This example demonstrates impressively the savings which can be achieved by employing the process according to the invention. The starting time of a paper machine is shortened to about one hour if the vibration potential is measured at the same time. Approximately $\frac{3}{4}$ tonnes of broke is produced. If one considers that the starting time hitherto varied between 1.5 and 4 hours and the machine had to be started 15 to 30 times in a year, the savings achieved can be considerable.

What we claim is:

1. A process for controlling the addition of retention agents to a fibrous suspensions, comprising the steps of: exposing a portion of the suspension of an ultrasonic field in a measuring cell having two electrodes which extend into the suspension and are spaced from each other by an odd multiple of half ultrasonic wavelengths of the ultrasonic field in the suspension; measuring the ultrasonic vibration potential generated by the ultrasonic field; and adding retention agents to the suspension in response to the magnitude of the measured ultrasonic vibration potential.

2. The process according to claim 1, wherein said suspension is a cellulose suspension comprising at least one of fillers, pigments and dyes.

3. A process according to claim 1 for the production of paper, wherein the potential between the electrodes is measured at least periodically when starting and during production.

4. The process according to claim 1, wherein the potential between the electrodes is employed in controlling the addition of flocculating agents which affect the zeta-potential of the suspension.

5. The process according to claim 1 or claim 4, wherein the potential between the electrodes is employed for the addition of retention agents to a continuously flowing stream of fibrous suspension and wherein the potential is measured continuously.

6. The process according to claim 1, wherein the suspension in the measuring cell is diluted.

* * * * *